United States Patent [19]

Sramek

[11] Patent Number: 5,068,099

[45] Date of Patent: Nov. 26, 1991

[54] HAIR SPRAY PACKAGE WITH LOW VOLATILE ORGANIC COMPOUND EMISSION

[75] Inventor: John A. Sramek, Wind Point, Wis.

[73] Assignee: S. C. Johnson & Son, Inc., Racine, Wis.

[21] Appl. No.: 464,796

[22] Filed: Jan. 16, 1990

[51] Int. Cl.$^5$ .................. A61K 7/11; A61K 9/12; B65D 83/14; B05B 1/00
[52] U.S. Cl. ....................... 424/47; 424/71; 424/81; 424/DIG. 1; 424/DIG. 2; 222/321; 222/394
[58] Field of Search ............ 424/47, 487, 78, 81, 424/501; 222/321

[56] References Cited

U.S. PATENT DOCUMENTS

| | | | |
|---|---|---|---|
| 1,767,023 | 10/1956 | Venus | 239/491 |
| 3,137,416 | 6/1964 | Shepherd et al. | 222/394 |
| 3,148,127 | 9/1964 | Marsh | 239/337 |
| 3,225,969 | 12/1965 | O'Donnell | 222/402.18 |
| 3,290,883 | 12/1966 | Giles et al. | 137/13 |
| 3,398,094 | 8/1968 | Blatz et al. | 252/8.55 |
| 3,544,258 | 12/1970 | Presant et al. | 222/192 |
| 3,893,597 | 7/1975 | Ewald | 222/402.22 |
| 4,007,005 | 2/1977 | Patel | 424/DIG. 1 |
| 4,019,657 | 4/1977 | Spitzer et al. | 222/136 |
| 4,051,983 | 10/1977 | Anderson | 222/321 |
| 4,124,149 | 11/1978 | Spitzer et al. | 222/402.19 |
| 4,141,472 | 2/1979 | Spitzer et al. | 222/189 |
| 4,192,862 | 3/1980 | Pengilly | 424/47 |
| 4,511,069 | 4/1985 | Kalat | 222/321 |
| 4,529,787 | 7/1985 | Schmidt et al. | 526/209 |
| 4,680,173 | 7/1987 | Burger | 424/47 |
| 4,871,529 | 10/1989 | Sramek | 424/47 |
| 4,874,604 | 10/1989 | Sramek | 424/47 |
| 4,935,224 | 6/1990 | Russo et al. | 424/47 |

OTHER PUBLICATIONS

"Aerosol Technology", The Center for Professional Advancement, M. A. Johnson, Course given at S. C. Johnson & Son, Inc., Racine, Wis., 12/16-17/86, 3 pages.
Product Information Bulletin: "SV-78 Vertical Action Valve", Summit Packaging Systems, Inc., Manchester, N.H., 4 pages, 12/81.
Datasheet: "Coster KRA 1" Continuous, High Filling Speed Valve 'Vapor Phase', Coster Technologie Speciali, S.P.A., Milan, Italy, 2 pages.
"Calmar, Inc., Fact Sheet Mark II", Brochure No. CPTG8416, Calmar, Inc., Watchung, N.J., 2 pages.
*Handbook of Aerosol Technology*, Second Edition, P. A. Sanders, VanNostrand Reinhold Co., N.Y., 1979, Ch. 6 & 9, pp. 85-115 and 145-164.
*The Aerosol Handbook*, 1st Ed., M. A. Johnsen, Wayne E. Dorland Co., Caldwell, N.J., 1972, Ch. 6, pp. 159-196.
"Aerosol Valves Up-to-Date", *Aerosol Age*, Apr. 1966, pp. 35, 38, 39, 46 and 116 and May, 1966, pp. 40D, 42, 44, 47-48 and 128-129.

*Primary Examiner*—Thurman K. Page
*Assistant Examiner*—Edward J. Webman

[57] ABSTRACT

The present invention relates to an aerosol hair spray package having reduced volatile organic compound emission during the useful life of the package. A hair spray composition (3, 25) is packaged in either a self-propelled aerosol hair spray package (1) or a pump spray hair spray package (20) containing a low delivery rate discharge means (6,23). The hair spray composition (3, 25) contains a combination of at least two polymers in weight ratios of 99:1 to 1:99 differing in weight average molecular weight by at least 1.5, one of which is required to have a number average molecular weight of at least 100,000. This blend of polymers combines with the low delivery rate discharge means—0.2-0.38 grams per second for the self-propelled hair spray package (1) and 0.06 to 0.012 grams per pump stroke for the pump spray hair spray package (20)—to provide an atomized hair spray composition having a volume mean particle size of 60±12 microns for package (12) and 73±13 microns for package (20). These packages are considerably smaller in size than conventional hair spray packages having higher discharge rates, but provide substantially the same number of uses per container as the larger size conventional hair spray packages, thus effecting reduced cost and environmental impact advantages.

18 Claims, 2 Drawing Sheets

HAIR SPRAY PACKAGE WITH LOW VOLATILE ORGANIC COMPOUND EMISSION

TECHNICAL FIELD

This invention relates to an improved hair spray composition dispensing package which provides reduced emission of volatile organic compounds through the use of a low delivery rate discharge means which is used to deliver a hair spray composition containing a combination of at least two polymers which act together to provide an atomized aerosol spray of a specific volume mean particle size. The packages may be in the form of a self-pressurized aerosol spray package or a pump-spray aerosol package.

BACKGROUND ART

In recent years there has been a great amount of concern over the contribution of volatile organic compounds to environmental pollution. Use of chlorofluorocarbons propellants in aerosol spray compositions have been banned in the United States for more than a decade. Emissions of hydrocarbons such as the volatile hydrocarbons used as aerosol spray propellants, for e.g., n-propane or isobutane, have come under increasing scrutiny as potential sources of air pollution as well as organic solvents commonly used in aerosol spray compositions such as ethanol. Thus, there is a need for improved aerosol spray compositions such as hair spray packages which permit the consumer to effectively style the hair, but which possess reduced emission of volatile organic compounds.

Alternative means for producing aerosol composition packages with reduced environmental impact have been proposed that use compressed gases such as carbon dioxide or nitrogen instead of volatile hydrocarbon propellants as well as the use of pump-spray packages which employ no propellant whatsoever. Special valves and pumps have been developed for use with such packages. The valves employed in packages pressurized with compressed packages tend to be complex since the pressure over the life of the can must be carefully regulated so that the gas is not expended prior to the time that the last of the composition is discharged from the package. Pump spray containers are more difficult to match with the compositions to be sprayed since there is no propellant and the pump spray unit itself must create adequate atomization of the hair spray composition. To work effectively, a hair spray composition must have a specific volume mean particle size.

If the volume mean particle size of the hair spray composition is too small, then the consumer tends to use a lot of hair spray to style the hair. Much of the fine particles are lost to the atmosphere creating a pollution problem and waste of the product. If the volume mean particle size of the atomized hair spray composition is too large, the composition tends to wet the hair and render it sticky. The styling of the hair may even be lost in such a case. This also tends to be wasteful of product. In either case, the hair spray composition package tends to have a short use life.

Several means for controlling the volume mean particle size of atomized hair spray compositions are known. For self-pressurized aerosol compositions, the orifices present in a typical aerosol valve can be varied in size to obtain a finer or coarser spray. Addition of a vapor tap orifice will cause the atomized hair spray composition to become finer and will reduce the discharge rate. The orifice size on the actuator button attached to the aerosol spray valve can also be modified to change the ultimate particles of the volume mean particle size of the hair spray composition. For example, U.S. Pat. No. 3,137,416 to Shepherd et al. teaches a composition for an aerosol dispenser consisting of two immiscible liquid phases.

This patent teaches the variation of the size of the vapor tap orifice and an aerosol spray valve to provide spray patterns from coarse wet sprays to finely atomized dry sprays. Examples 33 and 34 teach hair spray packages which have reduced spray rates of 24 grams/minute (0.4 grams/second) versus an average of 70 grams/minute (1.17 grams/second) for conventional anhydrous product and points out that the lower spray rate is very advantageous as it provides a longer lasting product. The sprays are described as finely atomized, dry sprays which had good hair holding properties and drying times. Example 34 employs several hair fixative polymers and a plasticizer as well as 21.2% water and 49.4% ethanol along with 25% isobutane as a propellant. The water is employed so that the hair spray composition becomes a two phase composition which is said to reduce the flammability of the hair spray product.

U.S. Pat. No. 4,192,862 to Pengilly teaches a hair spray containing a hair spray resin and a drag reducing agent which is typically a high molecular weight polymer which is used in a very small amount (less than about 0.3% by weight of the hair spray composition) to improve the holding power of a hair spray composition. From the examples given, it appears that the high molecular weight polymer being used as a drag reducing agent has an effect on the mean average particle size of the atomized hair spray composition being discharged from a pressurized aerosol spray composition package. Pengilly teaches that the inclusion of the drag reducing agent polymer can reduce the amount of hair spray inhaled into the lungs which he refers to as the "respirable fraction" of the product.

Neither of the above patents appear to address themselves to reducing the volatile organic content emission of hair spray composition packages.

SUMMARY DISCLOSURE OF INVENTION

One object of the present invention is to provide an improved hair spray package which provides the same spray characteristics and holding power of a conventional hair spray package, but accomplishes this with the use of less hair spray composition per application and thus results in reduced volatile organic compound emission to the atmosphere. The hair spray packages of the present invention use less composition to obtain the same hair styling characteristics and thus have the advantage of improving air quality while at the same time possessing reduced production costs because less composition is needed per package. Another advantage of the present invention is that the hair spray packages can be from one-half to one-third of the size of a conventional hair spray package while giving the same life as a larger conventional size package. This provides an economic advantage in that the packages themselves can be filled faster because they are smaller and the smaller packages use less raw material which must then be recycled or discarded.

These and other objects and advantages of the present invention are provided by an aerosol hair spray package employing a delayed delivery rate valve and an actuator button which discharge the hair spray composition at a rate of between 0.20 and 0.38 grams/second for a self-propelled aerosol spray composition, and more preferably, between 0.24 and 0.34 grams per second, and for a pump spray aerosol package, the rate of discharge is between 0.06 and 0.12 grams per pump stroke, and more preferably, is between 0.07 and 0.11 grams per stroke. Thus, less composition is provided to the hair over a unit period of time. To compensate for the adverse effects the reduction of discharge rate has on the volume mean particle size of the hair spray composition, a combination of at least two different hair fixative polymers in a weight ratio of 99:1 to 1:99 is employed wherein at least one of the hair fixative polymers has a weight average molecular weight of at least 100,000 and one of the hair fixative polymers differs from at least one other in weight average molecular weight by a factor of at least 1.5. The hair spray composition itself contains from about 1 to about 10 weight percent total hair fixative polymers where the amount and ratio of the hair fixative polymers present is such that in combination with the dispensing means selected, the volume mean particle size of 50% of the particles present in the spray being discharged are in the range of 60±12 microns for a self-propelled hair spray package and from 73±13 microns for a pump spray package. The solvents can be $C_2$-$C_4$ alcohols, water and mixtures thereof with no more than about 10% by weight of water for a self-propelled hair spray package and no more than about 25% water for a pump spray package. The self-propelled aerosol hair spray packages contain a propellant such as a volatile hydrocarbon such as isobutane and propane or a compressed gas such as nitrogen or carbon dioxide. Preferably, the hair spray compositions used in the present invention are homogeneous, one-phase compositions.

Because less solvent and, if present, organic propellant is used by the consumer when styling the hair, the consumer notices less solvent smell and the hair spray composition dries more quickly on the hair. By using the combination of polymers to control the hair spray particle size, the hair spray particles are optimized for application to the hair and wasteful overspray is minimized. Thus a smaller hair spray package having an optimized spray pattern is made available to the consumer at a lower cost and in a more convenient, smaller size, but possessing a useful product life which is comparable to a conventional hair spray package of from two to three times larger in volume. As noted, the containers of the present invention can be made lighter in weight than conventional hair spray packages and thus present less material to be disposed or recycled when the hair spray composition within the package is exhausted.

Another advantage of the present invention is that the combination of two or more hair fixative polymers to control the hair spray particle size permits the use of lower total hair fixative polymer solids content than is the case when a single hair fixative polymer is employed. This has a cost advantage in that less hair fixative polymer is required in a hair spray composition. It also provides a formulation advantage because the weight average molecular weight of any one hair fixative polymer is not as critical to the performance of the hair spray composition on the hair because variations in molecular weight of the polymer can be balanced by changing the ratio of the hair fixative polymers present.

BRIEF DESCRIPTION OF THE DRAWINGS

The above and other objects, features and advantages of the present invention will become apparent to those skilled in the art upon an examination of the following description and drawings which are merely illustrative of the present invention. In the Drawings.

BEST MODE FOR CARRYING OUT THE INVENTION

This invention relates to an improved self-propelled aerosol hair spray package comprising, in combination, a pressurized aerosol container sealed with an aerosol valve containing an actuator button having an exit orifice in flow communication with said valve and an alcoholic hair spray composition sealed within the container, the improvement comprising the valve being a low delivery rate valve capable of discharging the hair spray composition through the exit orifice at a rate of 0.20 to 0.38 grams per second and the hair spray composition comprises from about 1% to about 10% by weight of the total composition of at least two compatible hair fixative polymers in a weight ratio of 99:1 to 1:99, at least one of which polymers differs in weight average molecular weight from at least one other by a factor of at least 1.5 and at least one of the polymers has a weight average molecular weight of at least 100,000 wherein the ratio of the polymers and their total weight present in combination with the aerosol valve and actuator button on the package results in a discharged atomized aerosol spray having a volume mean particle size in the range of from about 60±12 microns, the remainder of the composition comprising a propellant and a solvent selected from the group consisting of $C_2$-$C_4$ alcohols, water and mixtures thereof, there being no more than about 10% by weight water present based upon the total weight of the hair spray composition.

This invention also relates to an improved pump aerosol hair spray package comprising, in combination, a container fitted with an aerosol pump spray unit containing an actuator button having an exit orifice in flow communication with an alcoholic hair spray composition sealed within the container, the improvement comprising the pump spray unit being a low delivery rate unit capable of discharging the hair spray composition through the exit orifice at a rate of 0.06 to 0.12 grams per pump stroke and the hair spray composition comprises from about 1% to about 10% by weight of the composition of at least two compatible hair fixative polymers in a weight ratio of at least 99:1 to 1:99, one of which polymers differs in weight average molecular weight from at least one other by a factor of at least 1.5 and at least one of the polymers has a weight average molecular weight of at least 100,000 wherein the ratio of the polymers and their total weight present in combination with the pump spray unit and actuator button on the package results in a discharged atomized aerosol spray having a volume mean particle size in the range of from about 73±13 microns, the remainder of the composition comprising a solvent selected from the group consisting of $C_2$14 $C_4$ alcohols, water and mixtures thereof, there being no more than about 25% water present based upon the total amount of hair spray composition present.

Figure 1:
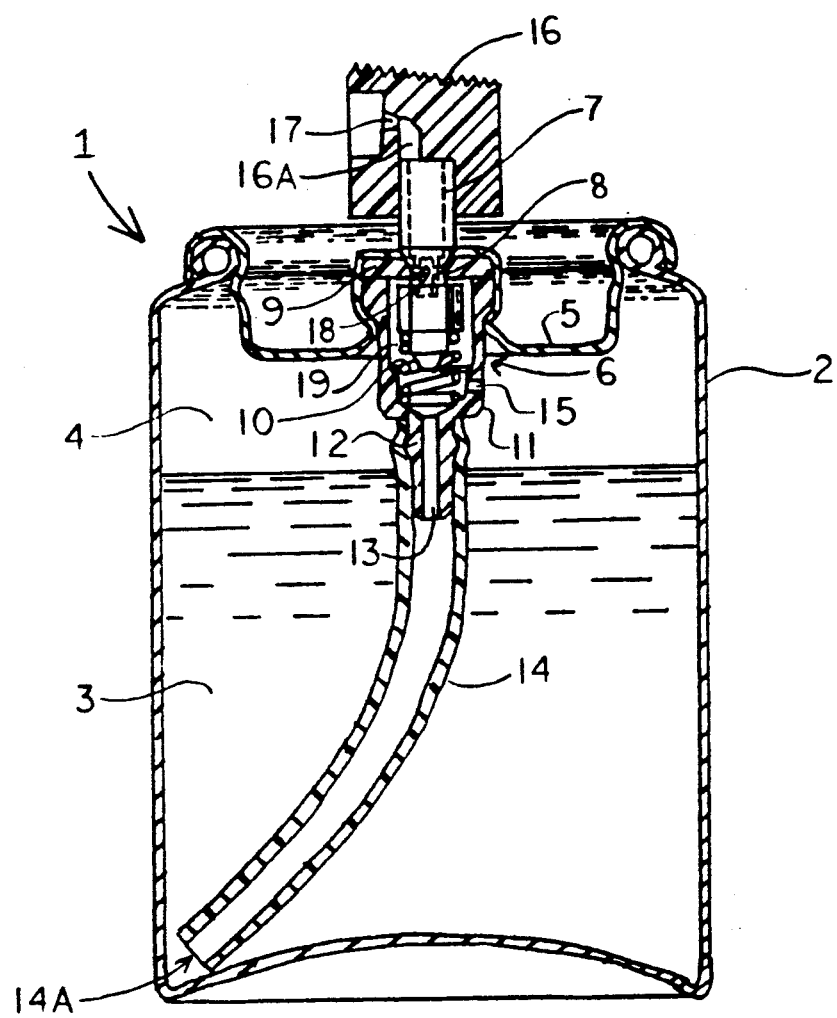
FIG. 1 is a cross-sectional view of a self-propelled hair spray package of the present invention.

FIG. 1 illustrates a self-propelled aerosol hair spray package which can be employed in the present invention. The package itself is conventional in construction and employs components which are readily available commercially from American National Can Company of Greenwich, Conn.; Continental Can Company, U.S.A., Inc., of Stamford, Conn.; The Precision Valve Company of Yonkers, N.Y.; Summit Packaging Systems, Inc., of Manchester, N.Y.; and Calmar, Inc., of Watchung, N.J. FIG. 1 illustrates one embodiment of an aerosol package which can be employed in the present invention. Thus, FIG. 1 shows self-propelled hair spray package 1 which is composed of lower container 2 which can be of glass, plastic or metal containing hair spray composition 3 above which is head space 4. Container 2 is sealed by means of mounting cup 5 which is typically of a metal material and may contain a gasket material (not shown) between the points where the rim of mounting cup 4 is in sealing contact with container 2. Mounting cup 5 contains valve member 6 for dispensing the hair spray composition. Valve member 6 comprises a hollow stem 7 with valve 8 normally seated against stem gasket 9 by means of spring 10 (as shown, the valve is in the closed or non-dispensing position). Surrounding the valve is a valve body 11 with tailpiece 12 having tailpiece orifice 13. Attached to tailpiece 12 is dip tube 14 extending into hair spray composition 3. Hair spray composition enters dip tube 14 by means of dip tube opening 14A. Valve body 11 also contains vapor tap orifice 15 for the separate entry of vapor from head space 4. On hollow stem 7 is mounted an actuator button 16 containing a passageway 16A in flow communication with hollow stem 7 containing actuator button orifice 17. When valve member 6 is actuated by pressing down button 16, valve 8 is unseated and the pressure of the propellant extrudes liquid hair spray composition 3 up dip tube 14 and through tailpiece orifice 13 into chamber 19 formed by valve body 11. Also, at the same time, vapor from head space 4 enters the chamber through vapor tap orifice 15 and the vapor and liquid aqueous phase are intermixed in chamber 19. This mixture enters hollow stem 7 through stem orifice 18, passes through passageway 16A, and is discharged from chamber 19 out through actuator button orifice 17 as an aerosol spray.

As is known in the art, one can increase or decrease the discharge rate of hair spray composition 3 from package 1 by altering the diameter of one or more of the orifices present in the hair spray package. Generally, suitable aerosol valves can be obtained by selecting orifices from the following sizes: stem orifice of from 0.010 inches (0.25 mm) to 0.016 inches (0.41 mm); tailpiece orifice of from 0.013 inches (0.33 mm) to 0.016 inches (0.41 mm) and vapor tap orifice of from 0.0055 inches (0.14 mm) to 0.012 inches (0.30 mm). In the present invention, a relatively low discharge rate of from about 0.20 to 0.38 grams/second is desirable with from about 0.24 to 0.34 grams/second being more preferred. The '416 Patent to Shepherd et al. teaches some of the design considerations involved in selecting useful combinations of orifice diameters.

For example, good results have been obtained using an actuator button having an actuator button orifice of 0.013 inches (0.33 mm) although a useful range is between from 0.010 to 0.020 inches (0.25 to 0.51 mm). Specific examples of valves and dip tubes which can be used in the present invention along with a mechanical breakup actuator button having a 0.013 inch (0.33 mm) actuator button orifice are:

| Example | A | B | C |
| --- | --- | --- | --- |
| Stem Orifice | 0.012" | 0.010" | 0.011" |
| | (0.3 mm) | (0.25 mm) | (0.28 mm) |
| Tailpiece Orifice | 0.016" | 0.013" | 0.013" |
| | (0.4 mm) | (0.33 mm) | (0.33 mm) |
| Vapor Tap Orifice | 0.012" | 0.0055" | 0.009" |
| | (0.3 mm) | (0.14 mm) | (0.23 mm) |
| Dip Tube Inner Diameter | 0.140" | 0.023" | 0.060" |
| | (3.56 mm) | (0.58 mm) | (1.5 mm) |

A preferred dip tube inner diameter is the one found in Example B noted above.

It is to be understood that the discharge rate of hair spray composition is also dependent upon the viscosity of the hair spray composition itself. As will be noted later, the non-volatile solids content of the hair fixative resin must also be matched with the specific valve, actuator button and dip tube selected to achieve the low discharge rate desired for use in the present invention. The discharge rate will also be dependent upon the pressure in the container as is well known in the art and can be adjusted by selection of propellant type, ratio of propellants, amount of propellant and initial pressurization level and procedure.

Figure 2:
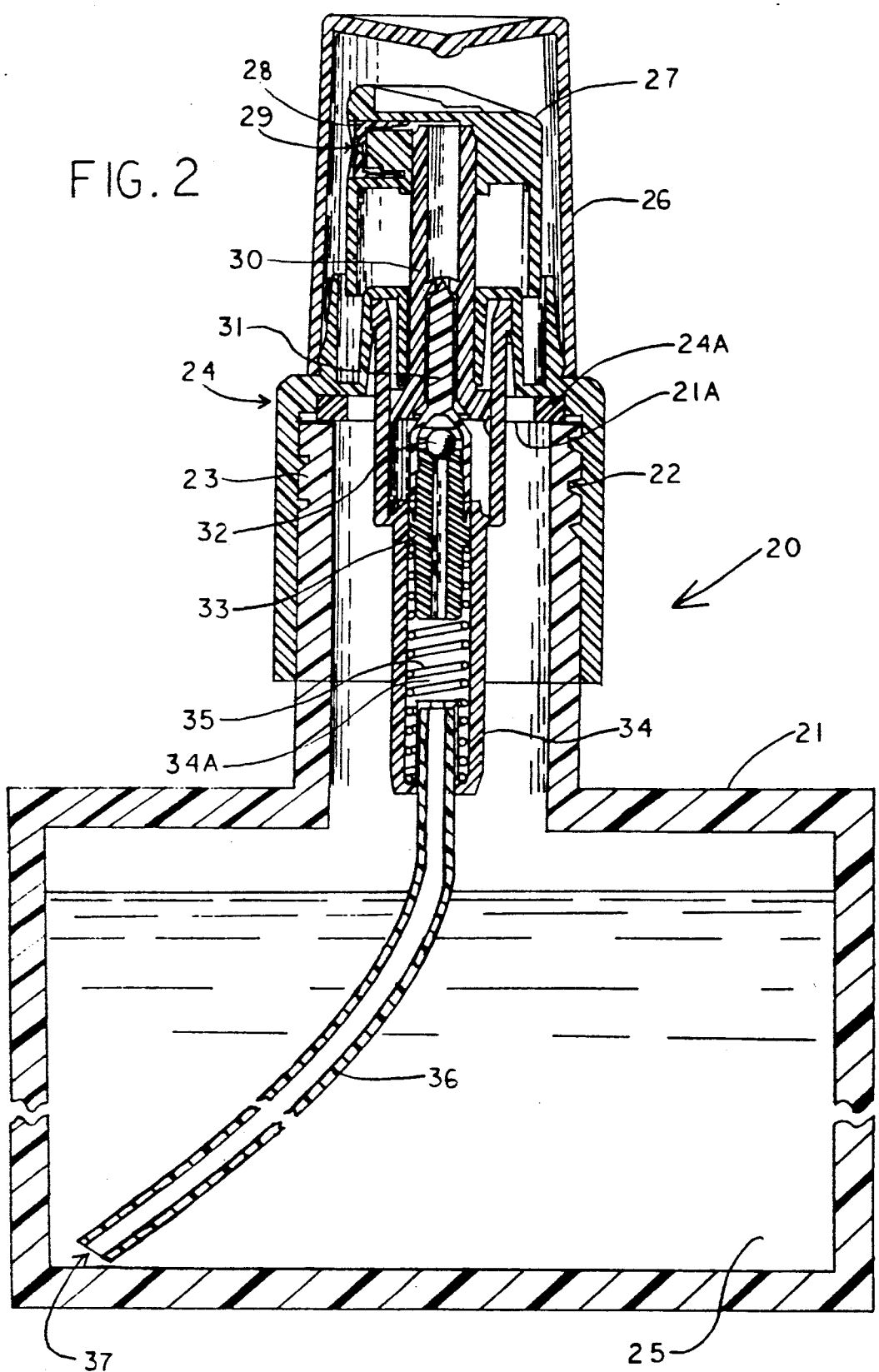
FIG. 2 is a cross-sectional view of a pump spray hair spray package of the present invention.

FIG. 2 illustrates a pump spray aerosol container of the type described in U.S. Pat. No. 4,051,983 to Anderson. Other pump spray packages can be employed provided that they are constructed to discharge from about 0.06 to 0.12 grams per stroke of the actuator button with a more preferred range being between about 0.07 and 0.11 grams per stroke of the hair spray composition to be delivered.

Referring to FIG. 2, pump spray hair spray package 20 is composed of container 21 having male threads 22 which are screwed into female threads 23 in pump spray unit 24 until the top of the opening 21A of container 21 seals against gasket 24A. Container 21 can be constructed of a suitable plastic, glass or metal material. Container 21 is filled with hair spray composition 25. A protective hood 26 is snapped over the top of pump spray unit 23 to prevent inadvertent pressure upon actuator button 27 from dispensing composition 25. Actuator button 27 contains orifice cup 28 with orifice 29 through which the hair spray composition is dispensed. Pump spray, unit 24 contains piston 30, a poppet 31 against which rests spherical valve 32 which may be a stainless steel ball. Seal valve 33 on poppet 31 assists in forming a lower piston chamber 34A in accumulator 34 in which stainless steel spring 35 is located. Dip tube 36 is sealingly engaged into accumulator 34 and the lower end of dip tube 36 extends to the bottom of container 21 to draw hair spray composition 25 into dip tube 36 through dip tube opening 37 when actuator button 27 is depressed. Orifice 29 is typically 0.012 inches (0.3 mm) in diameter although a useful range can be between from 0.005 inches (0.13 mm) to 0.030 inches (0.76 mm).

Although relatively high molecular weight acrylic resin hair fixative polymers are presently preferred for use in the present invention, it is believed that other hair fixative polymers which have been employed in the past for use in hair spray compositions can be employed provided that at least one of the polymers differs in weight average molecular weight from at least one other by a factor of at least 1.5 and provided that at least one of the hair fixative polymers has a weight average molecular weight of at least 100,000. To provide an effect on the volume mean particle size, the weight ratio of one polymer to another should be at least from 99:1 to 1:99 and more preferably, from 97:3 to 3:97. The weight average molecular weight is determined by reference to polystyrene standard reference polymers using gel permeation chromatography techniques. The determination of molecular weights by this procedure is well known to those of ordinary skill in the art and will not be described further.

The limiting factor on the molecular weight of the hair fixative polymers to be employed is based upon the viscosity in solution with a solvent comprising $C_2$-$C_4$ monoalcohols such as ethanol, n-propanol, isopropanol, n-butanol, isobutanol and tert-butanol, water and mixtures thereof. For practical reasons, the amount of water in a self-propelled aerosol hair spray composition is limited to no more than about 10% by weight of the total composition including propellant, to avoid the formation of emulsions due to the presence of volatile organic hydrocarbon propellants, if such are employed, and/or incompatibility of the hair fixative polymer being used with the water. Significant amounts of water are undesirable in hair spray composition since they also tend to wet the hair and cause it to lose style. For a pump spray composition, up to about 25% by weight of the composition can be water although it is often preferable to minimize the amount of water used in such compositions. To improve the compatibility of the hair fixative polymer with water, the hair spray resin can be neutralized with a base such as amines and ammonia. However, small amounts of water can sometimes help to reduce clogging of the aerosol valves by keeping polymers and salts in solution.

Ethanol and isopropanol are preferred as solvents with ethanol being most preferred. Hair spray compositions may also contain small amount of other solvents which do not provide the hair spray with an unpleasant odor. Thus, small amounts of other types of solvents such as methoxyethanol and 2-ethoxyethanol can also be included with the above described solvents.

In self-propelled aerosol hair spray compositions, a propellant can be included within the container to pressurize the composition. Examples of suitable propellants can be liquified lower hydrocarbons such as n-propane, n-butane, and isobutane as well as dimethyl ether, nitrogen and carbon dioxide. All propellants are used in sufficient quantities to provide a pressurizing amount of such propellant within the aerosol hair spray package. It is generally known that by increasing the amount of volatile organic propellant, the particle size of an aerosol spray becomes smaller. Thus at high propellant levels, the blend of hair fixative polymers should be selected so that the particle size of the atomized hair spray composition is within the desired ranges. Generally, propellants are employed as from about 10 to 80% by weight of the hair spray composition and, more preferably, between 15 and 40% by weight of the total composition.

The term "hair fixative polymer" as used herein and in the attached claims is intended to mean a film-forming polymer which is soluble in the solvents used in the hair spray composition and is capable of forming a film and holding the hair of a user in place after evaporation of the volatile components of the hair spray composition. Hair fixative polymers are well known articles of commerce and many such resinous polymers are available commercially which contain radicals which render the polymers anionic, cationic, amphoteric or nonionic in nature. To be useful in the present invention, at least one of the polymers employed must have a weight average molecular weight of at least 100,000 and at least one hair fixative polymer present must have a weight average molecular weight differing from at least one of the others present by a factor of at least 1.5, and more preferably, by a factor of about 2 to 10.

This difference in weight average molecular weight is exploited by using a hair fixative polymer of one molecular weight to modify the aerosol spray characteristics of the total hair spray composition due to its effect on the other hair fixative polymers present. For self-propelled aerosol hair spray packages, the desired volume mean particle size of the atomized spray is adjusted to be within $60 \pm 12$ microns while a pump spray package is desirably kept at $73 \pm 13$ microns.

By using a combination of hair fixative polymers (i.e., more than two can be employed although this is usually not desirable for reasons of economy and formulation simplicity), a lower overall level of total nonvolatile hair fixative polymer content can be employed in the hair spray compositions used than would be the case if only one hair fixative polymer is used with a low discharge rate dispensing means. To achieve the desired volume mean particle size, one can combine a major amount of a polymer that has a weight average molecular weight of greater than 100,000 with a minor amount of a second hair fixative polymer that is higher or lower in weight average molecular weight from at least one of the others present by a factor of at least 1.5 or the reverse by starting with a polymer of less than 100,000 weight average molecular weight.

In addition to its influence on hair spray particle size, the hair fixative polymer of greater than 100,000 molecular weight provides improved hair styling characteristics. In some formulations, all of the hair fixative polymers can have a weight average molecular weight of greater than 100,000.

Since high molecular weight polymers may act as thickening agents, their amount must be sufficiently low to permit an atomized aerosol spray to develop. The total amount of hair fixative polymer is between 1% and 10% of the total hair spray composition, including any propellant, and is preferably kept between about 2% and 6% depending upon the molecular weight of the polymers to minimize cost and to provide a hair spray composition having a viscosity that permits it to be discharged from the hair spray package in the form of an atomized spray composition having the above-described particle size. This can easily be evaluated by formulating a hair spray composition and spraying from the aerosol spray package to be used.

The present invention compares with conventional self-propelled aerosol compositions which typically use from about 1-3% by weight of hair fixative polymers in that the compositions used in the present invention typically use from about 2-6% hair fixative polymers (depending upon the molecular weight of the latter polymers since less can and often must be used for compositions containing a significant percentage of high molecular weight polymer). The discharge rate of current commercially available self-propelled aerosol hair spray packages is about 0.6-0.8 grams per second versus about 0.2-0.38 grams per second for the present invention. The container fill level for a typical size commercial self-propelled hair spray composition is from 7-9 fluid ounces (207-266 milliliters) versus about 2-4 fluid ounces (59-118 milliliters) for packages of the present invention. In the present invention, the nonvolatile solids content delivered to the hair per unit time or per pump stroke is adjusted to be substantially the same as that provided by a conventional hair spray package so that the smaller packages of the present invention last at least as long as the larger conventional hair spray packages.

The hair fixative polymers may be any of those known to be suitable for holding the hair in a desired style which fall within the above-described molecular weight ranges and ratios, are "compatible" with each other and soluble in the solvent system used. At present, blends of anionic acrylic terpolymers of methacrylic acid, butyl acrylate and ethyl methacrylate of different weight average molecular weights as described below are preferred as hair fixative polymers for use in the present invention. The term "compatible" as used herein and in the claims is intended to mean that each hair fixative polymer preferably has the same ionic charge or is neutral in ionic charge, is soluble in the solvent system selected, and does not form a precipitate when one polymer is mixed with the other polymer(s) selected. As a general guideline, it is preferable to select a hair fixative polymer for blending which has the same ionic charge as the other hair fixative polymers present in the hair spray composition or to use a nonionic hair fixative polymer. Thus, a hair spray composition using an anionic polymer would employ other anionic or nonionic hair fixative polymers while cationic polymers would employ other cationic or nonionic polymers. Depending upon the ionic charge of the polymer, amphoteric polymers could be used with either cationic or anionic polymers as well as with other amphoteric or nonionic polymers. Nonionic polymers could be used with any of the other classes of polymers noted if they are otherwise compatible.

Examples of anionic hair fixative polymers are copolymers of vinyl acetate and crotonic acid, terpolymers of vinyl acetate, crotonic acid and a vinyl ester of an alpha-branched saturated aliphatic monocarboxylic acid such as vinyl neodecanoate; and copolymers of methyl vinyl ether and maleic anhydride (molar ratio about 1:1) wherein such copolymers are 50% esterified with a saturated alcohol containing from 1 to 4 carbon atoms such as ethanol or butanol; and acrylic copolymers, terpolymers, etc., containing acrylic acid or methacrylic acid as the anionic radical-containing moiety and esters of acrylic or methacrylic acid with one or more saturated alcohols having from 1 to 22 carbon atoms such as methyl methacrylate, ethyl acrylate, ethyl methacrylate, n-butyl acrylate, t-butyl acrylate, n-butyl acrylate, t-butyl methacrylate, n-butyl methacrylate, n-hexyl acrylate, n-octyl acrylate, lauryl methacrylate and behenyl acrylate, glycols having from 1 to 6 carbon atoms such as hydroxypropyl methacrylate and hydroxyethyl acrylate, styrene, vinyl caprolactam, vinyl acetate, acrylamide, alkyl acrylamides and methacrylamides having 1 to 8 carbon atoms in the alkyl group such as methacrylamide, t-butyl acrylamide and n-octyl acrylamide, and other compatible unsaturated monomers. One specific example is the presently preferred emulsion polymerized terpolymer of methacrylic acid, n-butyl acrylate and ethyl methacrylate (e.g., in a weight percent ratio of 31:42:27, respectively). Another example is a terpolymer of tertiary-butyl acrylamide, acrylic acid and ethyl acrylate commercially sold by BASF Corporation under the name BASF UL-TRAHOLD(R) 8 (CTFA—Cosmetic, Toiletries and Fragrance Association—designation of Acrylate/Acrylamide Copolymer). Such anionic polymers are known in the art as can be seen from an examination of U.S. Pat. Nos. 3,405,084 to Bohac et al.; 3,577,517 to Kubot et al.; 3,577,518 to Shepherd et al.; 3,927,199 to Micchelli; 4,192,861 to Micchelli et al.; 4,192,862 to Pengilly et al.; 3,928,558 to Cheesman et al.; and 4,240,450 to Grollier et al. which are hereby incorporated by reference to teach such polymers.

Amphoteric polymers which can contain cationic groups derived from monomers such as t-butyl aminoethyl methacrylate as well as carboxyl groups derived from monomers such as acrylic acid or methacrylic acid can also be used in the present invention. One specific example of a amphoteric hair fixative polymer is one sold under the trademark AMPHOMER(R) by National Starch and Chemical Corporation which has the CTFA name of Octylacrylamide/Acrylates/-Butylaminoethyl Methacrylate Copolymer and is described in U.S. Pat. No. 4,192,861 as being a polymer of N-tert-octyl acrylamide, acrylic acid and t-butyl aminoethyl methacrylate. Examples of other amphoteric polymers are found in U.S. Pat. Nos. 3,726,288 to Nowak et al.; 3,981,987 to Link et al.; 4,237,253 to Jacquet et al.; and 4,358,567 to Hayama et al. which are hereby incorporated by reference to teach such polymers.

Examples of nonionic hair fixative polymers are homopolymers of N-vinylpyrrolidone and copolymers of N-vinylpyrrolidone with compatible nonionic monomers such as vinyl acetate and terpolymers of ethyl acrylate, butyl methacrylate and methyl methacrylate. Nonionic polymers containing N-vinylpyrrolidone in various weight average molecular weights are available commercially from GAF Corporation such as homopolymers of N-vinylpyrrolidone having an average molecular weight of about 630,000 sold by GAF under the tradename PVP K-90 and those having an average molecular weight of about 1,000,000 sold under the tradename of PVP K-120. More examples of such polymers are taught in U.S. Pat. Nos. 3,914,403, to Valan; and 4,378,345 to Okumura et al. which are hereby incorporated by reference.

Examples of cationic hair fixative polymers are copolymers of amino-functional acrylate monomers such as lower alkylaminoalkyl acrylate or methacrylate monomers such as dimethylaminoethyl methacrylate with compatible monomers such N-vinylpyrrolidone, vinyl caprolactam, or alkyl methacrylates such as methyl methacrylate and ethyl methacrylate and alkyl acrylates such as ethyl acrylate and n-butyl acrylate. Cationic hair fixative polymers containing N-vinylpyrrolidone are commercially available from GAF Corporation such as those sold under the tradenames of Copolymer 845 and Copolymer 937 (copolymers of N-vinylpyrrolidone and t-butylaminoethyl methacrylate of average molecular weight about 1,000,000) and GAFQUAT(R) 755 and 755N (quaternary ammonium polymers formed by the reaction of dimethyl sulfate and a copolymer of N-vinylpyrrolidone and dimethylaminoethyl methacrylate of average molecular weight about 1,000,000).

As is known in the art, those polymers which contain acidic groups and are insoluble in water are usually used in their neutralized, water-soluble or water-dispersible form. Suitable neutralizing agents which may be included in the hair spray compositions of the present invention are alkyl monoamines containing from about 2 to 22 carbon atoms such as triethylamine and laurylamine, and amino alcohols such as triethanolamine, 2-amino-2-methyl-1,3-propanediol and 2-amino-2-methyl-1-propanol. Other combinations of useful neutralizing agents are described in U.S. Pat. No. 4,874,604 to Sramek which is hereby incorporated by reference to teach such agents and their use in hair spray compositions. Similarly, cationic hair fixative polymers based on amines can be used in their acid salt form if it is desired to render them more water soluble.

In addition to the components described above, the hair spray compositions may additionally contain minor amounts of other ingredients commonly used in hair spray compositions such as perfumes, plasticizers, glossing agents, detackifying agents, combing aids, antistatic agents, conditioners, silicone additives such as those described in U.S. Pat. No. 4,871,529 to Sramek and the like. These types of additives are known to those of ordinary skill in the art and form no part of the present invention.

Industrial Applicability

Hair spray packages of the present invention are prepared by mixing solutions or dispersions of the hair fixative polymers together with the solvent to be used. This can be done in any order. Additives are then added although their order of addition is generally not critical either. Examples of the preparation of such compositions are given in the following Examples. After the hair spray composition is thoroughly mixed, it can be loaded directly into a pump spray container and sealed with a pump spray unit. It is preferred that the hair spray compositions be single phase and homogeneous to provide the user with a consistent product for application to the hair as a hair spray over the useful life of the hair spray package.

If a self-pressurized aerosol hair spray package using volatile hydrocarbon propellants is desired, it is preferable to have all of the components of the hair spray composition mixed and homogeneous prior to the addition of such propellants to the composition. The package can be sealed with an aerosol valve prior to the addition of propellant or after the hair spray composition is sealed inside if the propellant is added through the valve. Alternatively, a self-pressurized aerosol hair spray packages can be used where the hydrocarbon propellant is separated from the hair spray composition by using a two-compartment can of the type sold under the tradename SEPRO(R) can from American National Can Corporation. Similarly, compressed gas propellants can be added after the car is sealed. Another alternative is the use of an expanding bag self-pressurizing means such as that described in U.S. Pat. No. 4,513,884 to Magid in accordance with that patent.

Since the discharge means (i.e., aerosol valve or pump spray unit) for the package is selected with the hair spray composition in mind, the aerosol spray produced is optimized for application to the hair with minimal waste due to overspray. The consumer does not have to change spraying habits learned from using conventional larger aerosol spray packages since the spraying time is selected to be the same as that from conventional higher discharge rate hair spray packages. The packages of the present invention can be one-half to one-third as large as conventional packages while giving relatively the same number of uses. By optimizing the particle size, more hair fixative polymer gets to the hair. The hair looks and feels better because a more even film of hair fixative polymer spreads over the hair and the junctures between individual hair strands are more evenly coated and held together. Finally, one half to one third of the solvent, and if present, volatile hydrocarbon propellant, is emitted into the atmosphere because only one third to one half of the hair spray composition is used relative to a conventional size can for the same number of hair stylings. A smaller container also presents less cost to the manufacturer and less material to dispose and/or recycle.

The following Examples are provided to show various aspects of the present invention without departing from the scope and spirit of the invention. Unless otherwise indicated, all parts and percentages used in the Examples are by weight.

In the following Examples, a Malvern Laser Particle Analyzer, Model No. 2600C with a 300 mm lens, obtained from Malvern Instruments, England, (interfaced with a personal computer programmed to provide analyses of the data obtained) was employed to measure the volume mean particle size of atomized hair spray compositions sprayed from the hair spray packages tested by depressing and holding the spray orifice of the package's actuator button 8 inches (20.3 cm) from the center of the instrument's measuring beam. The volume mean particle size is reported in volume at 0.5 which means that on average, 50% of the volume of the particles measured are larger than the particle size reported and 50% of the volume of the particles are the same or smaller. Likewise, some of the examples report a volume particle size at 0.9 which means that on average, 90% of the volume of the particles were no larger than the particle size reported. The measurements were conducted at 75° F. (23.9° C.).

In the Examples which employed a pump spray package of the present invention, the pump spray unit used was a modified Calmar MARK II pump spray unit from Calmar, Inc. described in the '983 Patent to Anderson having a 0.012 inch (0.30 mm) spray orifice with a reduced pump stroke to provide a discharge rate of about 0.09 grams per stroke compared with a typical delivery rate of about 0.14–0.16 grams per stroke for the conventional MARK II spray unit. The piston size of the units used for the present invention was 0.1 cubic centimeter instead of the reported commercial 0.14 cubic centimeter size.

The following materials were used in the Examples:

Acrylic Polymer A was a terpolymer of 31% methacrylic acid, 42% n-butyl acrylate, and 27% ethyl methacrylate made by an aqueous emulsion polymerization process using a surfactant and no chain transfer agent wherein the resulting polymer (several different batches were used) had (via a gel permeation chromatographic technique using polystyrene standards) a weight average molecular weight (hereinafter "Mw") of about 700,000 and a sedimentation average molecular weight (defined in U.S. Pat. No. 4,529,787 to Schmidt et al. and hereinafter "Mz") of about 1,800,000. The polymer was used in the form of ar aqueous emulsion at 40% nonvolatile solids content. The emulsion polymerization surfactant used was sodium tridecyl ether sulfate, ammonium tridecyl ether sulfate or ammonium lauryl ether sulfate with the latter ammonium salts being more preferred since they tended to give emulsions with less tendency to clog the aerosol valves.

Acrylic Polymer B was an aqueous emulsion polymer of the same composition and nonvolatile solids content as Acrylic Polymer A, but was made using either 0.25% butyl mercaptopropionic acid ("BuMPA") or 0.34% iso-octyl mercaptopropionic acid ("IOMPA") as a chain transfer agent to obtain polymer batches having Mw about 140,000; and Mz about 330,000.

Acrylic Polymer C was an aqueous emulsion polymer of the same composition and nonvolatile solids content as Acrylic Polymer A, but was made using 0.68% IOMPA as a chain transfer agent to obtain polymer batches having Mw about 70,000; and Mz=140,000.

AMP-95 was 2-amino-2-methyl-1-propanol (95%) and 5% water from International Minerals & Chemicals Corp.

DOW CORNING(R) 345 was decamethyl cyclopentasiloxane and octamethyl cyclotetrasiloxane, 75% (CTFA name: Cyclomethicone) from Dow Corning Corporation.

LEXAMINE(R) L-13 was lauramidopropyl dimethylamine from Inolex Chemical Company.

SCHERCEMOL 105 was isodecyl neopentanoate from Scher Chemicals, Inc.

UNION CARBIDE SILWET(R) L-7602 was a trimethylsiloxy-endblocked polymer of dimethylsiloxy units and $(CH_3)SiO(C_xH_{2x})(OCH_2CH_2)_zOH$ units (CTFA name: Dimethicone Copolyol) where x was believed to be 3, the polymer contained 16% silicon content, and was reported to have a viscosity of from 70–130 centistokes ($0.7 \times 10^{-5}$ to $1.3 \times 10^{-4}$ meter per second), an average molecular weight of 3,000, density of 1.027 and a cloud point at 0.1% in water of less than 10° C.

EXAMPLES 1-2

These Examples describe the preparation and testing of 3.5 ounce (104 milliliter) size self-propelled aerosol hair spray packages of the present invention estimated to contain 24 average uses per container The first hair spray composition (Example 1) was prepared by first neutralizing Acrylic Polymer B (Mw=136,000 and Mz=322,000 using 0.25% BuMPA by adding the following together with stirring: 25.0 parts of Acrylic Polymer B, 1.334 parts of AMP-95, 2.0 parts of LEXAMINE L-13, and 71.666 parts of 200 proof denatured ethanol (hereinafter "Polymer Solution 1"). A second polymer solution was prepared as above by adding the following together with stirring: 50.0 parts of Acrylic Polymer C (0.68% IOMPA); 2.668 parts of AMP-95; 4.0 parts of LEXAMINE L-13; and 43.332 parts of 200 proof denatured ethanol (hereinafter "Polymer Solution 2"). "Additive Concentrate 1" was separately prepared by mixing the following together with stirring: 0.5 parts of UNION CARBIDE SILWET L-7602; 0.5 parts of DOW CORNING 345; 1.5 parts of fragrance; 5.0 parts of benzyl alcohol; 2.0 parts of SCHERCEMOL 105 and 90.5 parts of 200 proof denatured ethanol.

Example 1 had the following formulation: 10 parts of Additive Concentrate 1, 15 parts of Polymer Solution 1, 7.5 parts Polymer Solution 2, 47.5 parts of 200 proof denatured ethanol and 20 parts of isobutane. A homogeneous mixture of the first four ingredients (80 grams) was placed in a 202×314 lined tin plated steel aerosol container and using a 20 inch (50.8 cm) Hg vacuum, 37 cubic centimeters (20 grams) of isobutane was placed inside the container which was then sealed with an aerosol valve and dip tube of the type previously described above as Example C. A standard actuator button was then placed on the valve of the package which was a mechanical breakup, 2-piece button with a 0.013 inch (0.33 mm) button orifice (Seaquist No. 402-05480-13 Misty/Misty from Seaquist Valve, Division of Pittway Corporation).

The second hair spray composition was prepared by first preparing "Polymer Solution 3" using the same formula as for Polymer Solution 1, but using a batch of Acrylic Polymer A (Mw=800,000) in place of Acrylic Polymer B. Example 2 had the following formulation: 10 parts of Additive Concentrate 1, 12 parts of Polymer Solution 2, 6 parts Polymer Solution 3, 52 parts of 200 proof denatured ethanol and 20 parts of isobutane. This composition was packaged in the same type of hair spray package as described for Example 1 to obtain Example 2.

Each hair spray package was then tested with the following results. Upon initial testing after packaging, Example 1 exhibited a volume mean particle size of 50.6 microns with a discharge rate of 0.270 grams per second with a 3⅛ inch (7.94 cm) diameter spray pattern at 8 inches (20.3 cm) from the actuator button. Example 2 initially had a 70 micron volume mean particle size with a discharge rate of 0.298 grams per second with a 2.5 inch (6.35 cm) diameter spray pattern at 8 inches (20.3 cm) from the actuator button. After two months storage, both of the valves on the packages of Examples 1 and 2 had apparently become slightly clogged since the discharge rate upon testing had risen to 0.43 grams per second.

EXAMPLES 3-4

The hair spray composition used to prepare Example 3 employed "Polymer Solution 4" having the following formulation: 25.0 parts of Acrylic Polymer B (0.34% IOMPA), 1.0 parts of AMP-95, 2.0 parts of LEXAMINE L-13, and 72 parts of 200 proof denatured ethanol.

"Polymer Solution 5" was also prepared using 25 parts of Acrylic Polymer A, 1.0 parts of AMP-95, 2.0 parts of LEXAMINE L-13 and 72 parts of 200 proof denatured ethanol. The formulation for the hair spray composition used in Example 3 was 28.0 parts of Polymer Solution 4; 2.0 parts of Polymer Solution 5; 0.1 parts of UNION CARBIDE SILWET L-7602; 0.1 parts of DOW CORNING 345; 0.6 parts of benzyl alcohol; 0.2 parts of SCHERCEMOL 105; 0.1 parts of fragrance; 41.9 parts of 200 proof denatured ethanol; 2.0 parts of deionized water and 25.0 parts of isobutane. A homogeneous mixture of all ingredients except the isobutane (75 grams) was placed in a 202×314 lined tin plated steel aerosol container which was then sealed with an aerosol valve (and dip tube) of the type previously described as Example C. Using a 20 inch (50.8 cm) Hg vacuum, 25 grams of isobutane was filled through the valve into the container. The same standard actuator button used in Examples 1-2 was then placed on the package.

The formulation for the hair spray composition used in Example 4 was 17.0 parts of Polymer Solution 4; 3.0 parts of Polymer Solution 5; 0.1 parts of UNION CARBIDE SILWET L-7602; 0.1 parts of DOW CORNING 345; 0.4 parts of benzyl alcohol; 0.2 parts of SCHERCEMOL 105; 0.1 parts of fragrance; 2.0 parts of deionized water; 52.1 parts of 200 proof denatured ethanol; and 25.0 parts of isobutane. This hair spray composition is packaged into the same hair spray package as described for Example 3.

The hair spray package of Example 3 was tested and found to have a volume means particle size of 63.3 microns with a volume particle size at 0.9 of 125.4 microns and had a discharge rate of 0.27 grams per second. The instructions for use of this hair spray package are to style the hair as desired by spraying the composition onto the hair from a distance of 6–8 inches (15.2–20.3 cm) from the hair. The hair spray can also be used as a styling spray during styling of the hair.

EXAMPLE 5

This Example shows the production of a pump spray aerosol package of the present invention. To prepare Example 5, "Polymer Solution 6" was also prepared using 25.0 parts of Acrylic Polymer C (0.68% IOMPA); 1.0 parts of AMP-95; 2.0 parts of LEXAMINE L-13 and 72.0 parts of 200 proof denatured ethanol. "Polymer Solution 7" was also prepared using the same formulation as used for Polymer Solution 6, but Acrylic Polymer B (0.34% IOMPA) was used in place of the Acrylic Polymer C. The formulation for the hair spray composition used in Example 5 was 5.0 parts of Polymer Solution 6; 25.0 parts of Polymer Solution 7; 0.15 parts of UNION CARBIDE SILWET L-7602; 0.15 parts of DOW CORNING 345; 0.6 parts of benzyl alcohol; 0.2 parts of SCHERCEMOL 105; 0.15 parts of fragrance; 10.0 parts of deionized water; and 58.75 parts of 200 proof denatured ethanol.

This formulation was placed into a 3.5 ounce (104 milliliter) screw top container onto which a modified MARK II pump spray unit was screwed to obtain the hair spray package of Example 5. The instructions for using this pump spray package are to style the hair as desired holding the package from 6–8 inches (15.2–20.3 cm) from the hair while using quick, full strokes on the actuator button. If the pump unit should become clogged, rinse it under warm water until it becomes unclogged. The hair spray can also be used as a styling spray during styling of the hair.

The volume mean particle size obtained for Example 5 was 64.0 microns and the volume particle size at 0.9 was 102.6 microns.

EXAMPLES 6–8

These Examples give further examples of hair spray compositions which can be placed in pump spray aerosol containers of the type described in Example 5 to obtain pump spray hair spray packages of the present invention.

The following composition was placed in the same type of hair spray package as described in Example 5 to obtain the hair spray package of Example 6: 28.5 parts of Polymer Solution 6; 1.5 parts of Polymer Solution 5; 0.15 parts of UNION CARBIDE SILWET L-7602; 0.15 parts of DOW CORNING 345; 0.6 parts of benzyl alcohol; 0.2 parts of SCHERCEMOL 105; 0.15 parts of fragrance; 10.0 parts of deionized water; and 58.75 parts of 200 proof denatured ethanol. The volume mean particle size obtained upon spraying from this hair spray package was 75.5 microns and the volume particle size at 0.9 for this hair spray package was 130 microns.

The following hair spray composition was prepared and placed in the pump spray aerosol package of the type described in Example 5 to obtain a hair spray package of the present invention: 27.0 parts of Polymer Solution 6; 3.0 parts of Polymer Solution 5; 0.15 parts of UNION CARBIDE SILWET L-7602; 0.15 parts of DOW CORNING 345; 0.6 parts of benzyl alcohol; 0.2 parts of SCHERCEMOL 105; 0.15 parts of fragrance; 10.0 parts of deionized water and 58.75 parts of 200 proof denatured ethanol. The pump spray aerosol hair spray package of Example 7 was found to produce a spray with a volume mean particle size of 82.4 microns and a volume particle size at 0.9 of 141 microns upon spraying.

The following hair spray composition is placed in a pump spray aerosol hair spray container package of the type described in Example 5 to produce the hair spray package of Example 8: 1.0 parts of Polymer Solution 5; 19.0 parts of Polymer Solution 7; 0.1 parts of UNION CARBIDE SILWET L-7602; 0.1 parts of DOW CORNING 345; 0.4 parts of benzyl alcohol; 0.1 parts of SCHERCEMOL 105; 0.1 parts of fragrance; 10.0 parts of deionized water and 69.2 parts of 200 proof denatured ethanol.

EXAMPLES 9–10

These Examples demonstrate a small-scale salon test of an aerosol hair spray package of the present invention (Example 9) versus a hair spray package containing only 1 polymer in the hair spray composition (comparative Example 10). "Additive Concentrate 2" had the following formulation: 1.0 parts of UNION CARBIDE SILWET L-7602; 1.0 parts DOW CORNING 345; 0.75 parts of fragrance; 6.0 parts of benzyl alcohol; 2.0 parts of SCHERCEMOL 105; and 89.25 parts 200 proof denatured ethanol.

To prepare Example 9: "Polymer Solution 8" was prepared having the following formulation: 25.0 parts of Acrylic Polymer B (0.34% IOMPA); 1.0 part of AMP-95; 2.0 parts of LEXAMINE L-13; and 72.0 parts of 200 proof denatured ethanol. The following hair spray composition was packaged into the same aerosol container type with the same type of valve and actuator buttons described for Examples 1–2 to prepare the hair spray package of Example 9: 28.0 parts Polymer Solution 8; 10.0 parts of Additive Concentrate 2; 2.0 parts of Polymer Solution 3; 33.0 parts of 200 proof denatured ethanol; 2.0 parts of deionized water; and 25 parts of isobutane.

The hair spray package of Example 10 was prepared by adding the following hair spray formulation to the same packages described for Examples 1–2: 10 parts of Additive Concentrate 1; 30 parts of Polymer Solution 1; 40 parts of 200 proof denatured ethanol; and 20 parts of isobutane.

One hair spray package of Example 9 was found to have a discharge rate of 0.31 grams per second of hair spray composition (after partial use) having a volume mean particle size of 59.0 microns and a volume particle size at 0.9 of 108.4 microns.

One hair spray package of Example 10 was found to have a discharge rate of 0.279 grams per second with a volume mean particle size of 53.5 microns.

Other hair spray packages used in the test were chosen at random and also evaluated for discharge rate and volume mean particle size with the following results: Example 9 for two different hair spray packages: discharge rates of 0.26 and 0.27 grams per second with volume mean particle sizes of 59.0 and 61.7 microns and volume particle sizes at 0.9 of 108.4 and 116.5 microns, respectively. Two randomly selected hair spray packages of Example 10 had discharge rates of 0.23 and 0.30 grams per second with volume mean particle sizes of 58.4 and 59.6 microns and volume particle sizes at 0.9 of 115.5 and 103.5, respectively.

Professionally-trained hair stylists were used to evaluate the hair spray packages of Examples 9 and 10 in blind-labeled containers on the hair of 19 volunteer subjects. Although this sample size is small, the hair stylists slightly preferred Example 9 as being a better working spray. Each of the 19 volunteer subjects was asked to evaluate which of the hair spray packages they preferred upon using the product at home and evaluating it 6-8 hours later. In terms of hair "Body", ten subjects preferred Example 9, one subject preferred Example 10 and eight subjects judged the two Examples to be equal. In terms of "Soft Feel" of the hair after spraying, five subjects preferred Example 9 (some remarked that the hair felt coated), seven subjects preferred Example 10 and seven judged both Examples to be equal. In terms of "hold", eight preferred Example 9, one preferred Example 10 and ten judged both to be equal. "Overall", nine subjects preferred Example 9, three subjects preferred Example 10 and seven subjects judged both Examples to be equal. During the testing, one can of Example 10 completely clogged during the testing.

What I claim is:

1. An improved self-propelled aerosol hair spray package comprising, in combination, a pressurized aerosol container sealed with an aerosol valve containing an actuator button having an exit orifice in flow communication with said valve and an alcoholic hair spray composition sealed within the container, the improvement comprising the valve being a low delivery rate valve capable of discharging the hair spray composition through the exit orifice at a rate of 0.20 to 0.38 grams per second and the hair spray composition comprises from about 1% to about 10% by weight of the total composition of at least two compatible hair fixative polymers in a weight ratio of at least 99:1 to 1:99, wherein one polymer present differs in weight average molecular weight from at least one other by a factor of at least 1.5 and at least one polymer present has a weight average molecular weight of at least 100,000 wherein the polymers and their total weight present in combination with the aerosol valve and actuator button on the package results in a discharged atomized aerosol spray having a volume means particle size in the range of from about 60±12 microns, the remainder of the composition comprising both a solvent selected from the group consisting of $C_2$-$C_4$ alcohols, water and mixtures thereof, there being no more than about 10% by weight water present based upon the total weight of the hair spray composition, and a propellant, wherein the package gives relatively the same number of uses, but has from about one-third to one-half of the volume of hair spray composition, as does a second package having (a) at least twice the discharge rate, (b) a volume mean average particle size in the same range, and (c) about one-half by weight of the hair fixative polymer content.

2. The package of claim 1 wherein the ratio of hair fixative polymers of differing molecular weight is between 97:3 to 3:97 and the difference factor between the molecular weights of the hair fixative polymers is in the range of from 2 to 10.

3. The package of claim 2 wherein at least one of the hair fixative polymers is an anionic addition polymer comprising polymerized anionic carboxyl group units selected from the group consisting of acrylic acid, methacrylic acid, or mixtures thereof.

4. The package of claim 3 wherein the anionic polymer comprises polymerized units selected from the group consisting of an ester of a saturated alcohol having from 1 to 22 carbon atoms and an acid selected from the group consisting of acrylic acid and methacrylic acid.

5. The package of claim 4 wherein each hair fixative polymer is a terpolymer of methacrylic acid, n-butyl acrylate and ethyl methacrylate.

6. The package of claim 1 wherein the exit orifice of the actuator button is from 0.010 inches (0.25 mm) to 0.020 inches (0.51 mm) and the aerosol valve has a stem orifice of from 0.010 inches (0.25 mm) to 0.016 inches (0.41 mm), a tailpiece orifice of from 0.013 inches (0.33 mm) to 0.016 inches (0.41 mm), and, a vapor tap orifice of from 0.0055 inches (0.14 mm) to 0.012 inches (0.30 mm).

7. The package of claim 6 wherein hair spray is discharged from the exit orifice at a rate of between 0.24 and 0.34 grams per second.

8. An improved pump aerosol hair spray package comprising, in combination, a container fitted with an aerosol pump spray unit containing an actuator button having an exit orifice in flow communication with an alcoholic hair spray composition sealed within the container, the improvement comprising the pump spray unit being a low delivery rate unit capable of discharging the hair spray composition through the exit orifice at a rate of 0.06 to 0.12 grams per pump stroke and the hair spray composition comprises from about 1% to about 10% by weight of the composition of at least two compatible hair fixative polymers in a weight ratio of at least 99:1 to 1:99, wherein one polymer present differs in weight average molecular weight from at least one other by a factor of at least 1.5 and at least one polymer present has a weight average molecular weight of at least 100,000 wherein the polymers and their total weight present in combination with the pump spray unit and actuator button on the package results in a discharged atomized aerosol spray having a volume mean particle size in the range of from about 73±13 microns, the remainder of the composition comprising a solvent selected from the group consisting of $C_2$-$C_4$ alcohols, water and mixtures thereof, there being no more than about 25% water present based on the total amount of hair spray composition present wherein the package gives relatively the same number of uses, but has from about one-third to one-half of the volume of hair spray composition, as does a second package having (a) a discharge rate of from about 0.14 to 0.16 grams/per stroke, (b) a volume mean average particle size in the same range, and (c) about one-half by weight of the hair fixative polymer content.

9. The package of claim 8 wherein the ratio of hair fixative polymers of differing molecular weight is between 97:3 to 3:97 and the difference factor between the molecular weights of the hair fixative polymers is in the range of from 2 to 10.

10. The package of claim 9 wherein at least one of the hair fixative polymers is an anionic addition polymer comprising polymerized anionic carboxyl group units selected from the group consisting of acrylic acid, methacrylic acid, or mixtures thereof.

11. The package of claim 10 wherein the anionic polymer comprises polymerized units selected from the group consisting of an ester of a saturated alcohol having from 1 to 22 carbon atoms and an acid selected from the group consisting of acrylic acid and methacrylic acid.

12. The package of claim 11 wherein each hair fixative polymer is a terpolymer of methacrylic acid, n-butyl acrylate and ethyl methacrylate.

13. The package of claim 8 wherein hair spray is discharged from the exit orifice at a rate of between 0.07 and 0.11 grams per stroke.

14. The package of claim 8 wherein the solvent is ethanol and the hair spray composition contains no more than about 10% water.

15. The package of claim 1 wherein each hair fixative polymer has a weight average molecular weight of at least 100,000.

16. The package of claim 15 wherein the ratio of said hair fixative polymers of differing molecular weight is between 97:3 to 3:97, the difference factor between the molecular weights of any two of the hair fixative polymers present is in the range of from 2 to 10, and the hair fixative polymers comprise from about 2% to 6% of the total composition.

17. The package of claim 8 wherein each hair fixative polymer has a weight average molecular weight of at least 100,000.

18. The package of claim 17 wherein the ratio of said hair fixative polymers of differing molecular weight is between 97:3 to 3:97, the difference factor between the molecular weights of any two of the hair fixative polymers present is in the range of from 2 to 10, and the hair fixative polymers comprise from about 2% to 6% of the total composition.

* * * * *